United States Patent
Melis et al.

(10) Patent No.: US 8,993,290 B2
(45) Date of Patent: Mar. 31, 2015

(54) CONTINUOUS DIFFUSION BASED METHOD OF CULTIVATING PHOTOSYNTHETIC MICROORGANISMS IN A SEALED PHOTOBIOREACTOR TO OBTAIN VOLATILE HYDROCARBONS

(75) Inventors: Anastasios Melis, El Cerrito, CA (US);
Fiona Bentley, Berkeley, CA (US);
Hsu-Ching Chen Wintz, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/113,021

(22) PCT Filed: Apr. 20, 2012

(86) PCT No.: PCT/US2012/034544
§ 371 (c)(1),
(2), (4) Date: Dec. 19, 2013

(87) PCT Pub. No.: WO2012/145692
PCT Pub. Date: Oct. 26, 2012

(65) Prior Publication Data
US 2014/0106422 A1  Apr. 17, 2014

Related U.S. Application Data

(60) Provisional application No. 61/477,896, filed on Apr. 21, 2011.

(51) Int. Cl.
| | | |
|---|---|---|
| *C12P 5/00* | (2006.01) | |
| *C12N 1/12* | (2006.01) | |
| *C12P 7/04* | (2006.01) | |
| *C12P 7/06* | (2006.01) | |
| *C12P 7/16* | (2006.01) | |
| *C12P 7/24* | (2006.01) | |

(52) U.S. Cl.
CPC . *C12P 5/007* (2013.01); *C12N 1/12* (2013.01); *C12P 7/04* (2013.01); *C12P 7/065* (2013.01); *C12P 7/16* (2013.01); *C12P 7/24* (2013.01); *Y02E 50/10* (2013.01); *Y02E 50/17* (2013.01)
USPC ........................................ 435/167

(58) Field of Classification Search
USPC .......................................... 435/167
IPC ................................ C12P 5/00,7/065
See application file for complete search history.

(56) References Cited

U.S. PATENT DOCUMENTS

| | | | |
|---|---|---|---|
| 8,324,442 B2 * | 12/2012 | McPhee | 585/810 |
| 2008/0160591 A1 | 7/2008 | Willson et al. | |
| 2008/0178739 A1 | 7/2008 | Lewnard et al. | |
| 2010/0068801 A1 | 3/2010 | Woods et al. | |
| 2011/0065157 A1 * | 3/2011 | Gorny et al. | 435/160 |
| 2012/0065439 A1 | 3/2012 | Siemer et al. | |
| 2014/0030785 A1 * | 1/2014 | Kailas et al. | 435/167 |
| 2014/0134672 A1 * | 5/2014 | Tuttman et al. | 435/47 |

FOREIGN PATENT DOCUMENTS

| | | |
|---|---|---|
| WO | WO 2008/003078 A2 | 1/2008 |
| WO | WO 2008/137092 A2 | 11/2008 |
| WO | WO 2010/127290 A2 | 11/2010 |
| WO | WO 2011/003024 A2 | 1/2011 |

OTHER PUBLICATIONS

Pulz O. Photobioreactors: Production Systems for Phototrophic Microorganisms. Applied Microbiol Biotechnol 57(3)287-293, Oct. 2001.*
Bentley, F., et al., "Diffusion-based process for carbon dioxide uptake and isoprene emission in gaseous/aqueous two-phase photo-bioreactors by photosynthetic microorganisms," *Biotechnology and Bioengineering* vol. 109(1), pp. 100-109 (Online: Aug. 9, 2011).
Ezeji, T., et al., "Butanol fermentation research: upstream and downstream manipulations," *The Chemical Record*, vol. 4(5), pp. 305-314 (2004).
Younesi, H., et al., "Ethanol and acetate production from synthesis gas via fermentation processes using anaerobic bacterium, *Clostridium ijungdahlii*," *Biochemical Engineering Journal*, vol. 27(2), pp. 110-119 (2005).
PCT International Search Report and Written Opinion for PCT/US2012/034544, mailed Oct. 31, 2012, 12 pgs.

* cited by examiner

*Primary Examiner* — Ralph Gitomer
(74) *Attorney, Agent, or Firm* — Kilpatrick Townsend & Stockton LLP

(57) ABSTRACT

This invention relates to methods of obtaining volatile hydrocarbons produced by photosynthetic microorganisms using a two-phase gaseous/aqueous bioreactor.

22 Claims, 11 Drawing Sheets

CONTINUOUS DIFFUSION BASED METHOD OF CULTIVATING PHOTOSYNTHETIC MICROORGANISMS IN A SEALED PHOTOBIOREACTOR TO OBTAIN VOLATILE HYDROCARBONS

CROSS-REFERENCE TO RELATED APPLCIATIONS

This application is a US National Phase of PCT/US2012/034544, filed Apr. 20, 2012, which claims benefit of U.S. provisional application No. 61/477,896, filed Apr. 21, 2011, each of which is herein incorporated by reference for all purposes.

BACKGROUND OF THE INVENTION

Isoprenoids, also referred to as terpenoids, constitute the largest and most diverse group of naturally occurring organic chemicals, with more than 25,000 different member compounds. The smallest isoprenoid is isoprene ($C_5H_8$) a volatile five-carbon hydrocarbon with considerable commercial potential, as it is feedstock in the synthetic chemistry industry, where it is used to manufacture products ranging from rubber to adhesives and perfumes. There is also potential for isoprene to be developed as a renewable biofuel, where oligomerization of isoprene units may generate second order fuel molecules, suitable for use as supplements of gasoline, jet fuel, and diesel. Currently, the industrial supply of isoprene is limited to petrochemical sources. Sustained availability of these resources is being questioned by the increasing global demand for energy and synthetic chemistry feedstock. Accordingly, there is a need to develop methods for the renewable production, sequestration and trapping of volatile isoprene hydrocarbons in processes that can be scaled-up for industrial application.

A variety of herbaceous, deciduous and conifer plants naturally produce isoprene via the process of leaf photosynthesis. Heat-stress of the plant is a prerequisite for the induction of isoprene synthase (IspS) gene expression and enzymatic activity (Sasaki et al. 2007; Sharkey et al., 2008). As a small hydrophobic and volatile molecule, isoprene easily passes though chloroplast and cellular membranes and is released into the atmosphere though the stomata of leaves (Sharkey and Yeh, 2001; Sharkey et al., 2008).

Given the volatile nature of isoprene (boiling point=34.1° C.), it is impractical to attempt to harvest this hydrocarbon from herbaceous, deciduous or conifer plants. Microorganisms, however, can be cultivated in fully enclosed bioreactors that offer advantages in product containment and sequestration. Although some microorganisms naturally produce isoprene (Kuzma et al., 1995) the quantities are small. Overexpression of a plant IspS gene in a photosynthetic or non-photosynthetic microorganism can effectively endow the property of isoprene production from the cell's own metabolism (Lindberg et al., 2010; Whited et al., 2010; Miller et al., 2001). Isoprene synthase (IspS) has been expressed in photosynthetic cyanobacteria and microalgae (see also, Lindberg et al. 2010, WO/2008/003078 and WO2008/137092).

There is also a need for additional methods for the renewable production, sequestration and trapping of other volatile compounds such as alcohols and aldehydes.

BRIEF SUMMARY OF THE INVENTION

The present invention is based, in part, on the discovery and application of a diffusion-driven process in gaseous/aqueous two-phase photobioreactors for carbon dioxide uptake and isoprene plus oxygen emission by photosynthetic microorganisms (microalgae or cyanobacteria). Methods and composition, disclosed herein for the diffusion-driven exchange of $CO_2$ with a volatile hydrocarbon, e.g., isoprene, plus oxygen, can be scaled-up to mass culture conditions for the commercial production and exploitation of a volatile hydrocarbon, such as isoprene. The invention further discloses methods for the subsequent separation of the photosynthetically-generated isoprene from oxygen.

Thus, in one aspect, the invention provides a method of cultivating photosynthetic microorganisms in a sealed photobioreactor to obtain a volatile product of photosynthesis generated by the microorganisms, the method comprising culturing a photosynthetic microorganism in a sealed photobioreactor, wherein the photobioreactor contains a lower aqueous phase comprising the photosynthetic microorganism, and an upper gaseous phase, wherein the upper gaseous phase has a $CO_2$ concentration of at least 10%; introducing additional CO2 into the upper gaseous phase when the $CO_2$ concentration drops below 10%; and collecting the volatile product that is sequestered into the gaseous phase and displaced by the additional $CO_2$. In some embodiments, the photosynthetic microorganism is a recombinant organism that expresses at least one heterologous gene that produces the volatile hydrocarbon, such as isoprene. In some embodiments, the microorganism expresses an isoprene synthase gene. In some embodiments, the microorganism is a cyanobacteria or a green microalgae. In some embodiments, the volatile compound is an alcohol, such as ethanol, butanol or isobutanol. In some embodiments, the volatile compound is an aldehyde such as acetaldehyde, butyraldehyde, or isobutyraldehyde.

In some embodiments, the volume ratio of the gaseous phase to the aqueous phase is in the range of from about 1:9 to about 9:1. In some embodiments, the volume ratio of the gaseous phase to the aqueous phase is in the range of from about 4:6 to about 6:4.

In some embodiments, the step of introducing additional $CO_2$ into the upper gaseous phase occurs when the CO2 concentration is below 50%.

In some embodiments of the method of the invention, the volatile product is isoprene and the step of collecting the volatile product comprises passing the contents of the gaseous phase displaced by the additional $CO_2$ or displaced by a stream of air, through a cooled condenser and through a cooled hydrophobic solvent, thereby retaining the isoprene and separating it from the photosynthetically-generated $O_2$. In some embodiments, the hydrophobic solvent comprises methanol, ethanol, butanol, hexane, heptane, octane, or dodecane.

DETAILED DESCRIPTION OF THE INVENTION

Introduction

Figure 1:
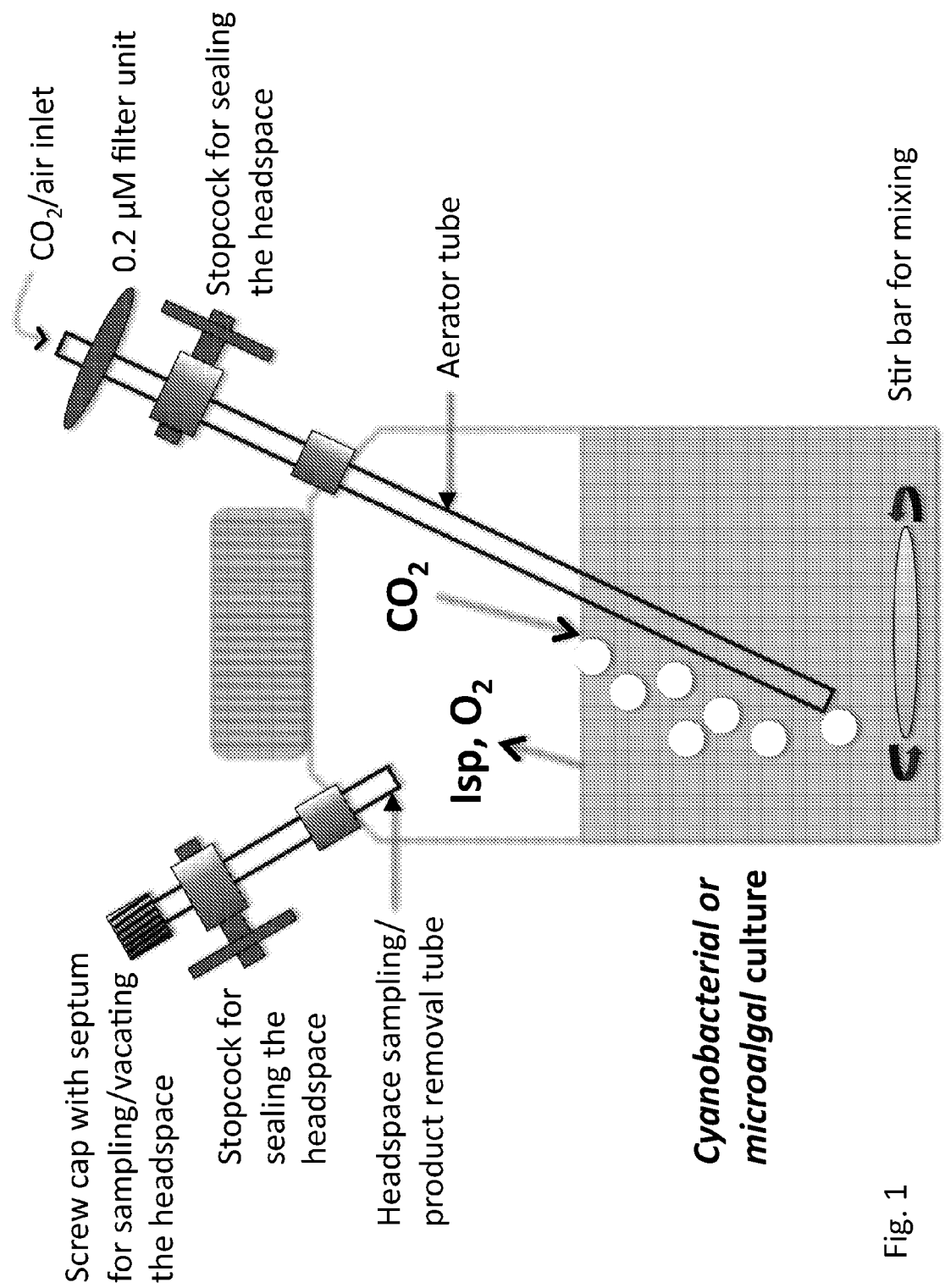
FIG. 1 depicts an example of a fed-batch bioreactor for diffusion-based $CO_2/O_2$ gas exchange and volatile hydrocarbons production and sequestration. A 100% $CO_2$ gas stream was slowly fed into the gaseous/aqueous two-phase bioreactor via the aerator tube to fill the reactor headspace. The $CO_2$ is applied either by bubbling at the bottom of the liquid phase (FIG. 1), or as a stream of air at the surface of the liquid phase. The reactor is then sealed to retain $CO_2$ in the headspace. Efficient uptake and assimilation of headspace $CO_2$ by the cells occurred by diffusion from the gaseous phase to the liquid phase and was concomitantly exchanged for photosynthetically produced $O_2$ and isoprene during cell photoautotrophic growth. Accumulation of isoprene over time took place in the sealed bioreactor headspace. Slow continuous mechanical mixing of the liquid phase was employed to keep cells suspended and to promote balanced cell illumination and gaseous $CO_2$ diffusion in the culture. Gas samples were taken from the headspace though the septum of the sampling/product removal tube for isoprene concentration analysis by gas chromatography (GC).

Photosynthesis for the generation of fuels and chemicals from cyanobacteria and microalgae offers the promise of addressing currently emerging global challenges for the renewable generation of fuels and synthetic chemistry feedstock. The invention is based, in part, on the discovery and application of methods and compositions for the use of a sealed gaseous/aqueous two-phase photobioreactor for the photosynthetic generation of volatile hydrocarbons, such as isoprene ($C_5H_8$) hydrocarbons. The invention operates on the principle of diffusion of $CO_2$ from the gaseous headspace into the microalgal or cyanobacterial-containing aqueous phase, followed by $CO_2$ uptake, photosynthetic assimilation, and hydrocarbon production by these photosynthetic microorganisms, which in some embodiments, are microalgae or cyanobacteria that are genetically engineered to produce the volatile hydrocarbon. Volatile hydrocarbons are emitted from the aqueous phase and are sequestered into the gaseous headspace. Periodic replacement (flushing) of the volatile hydrocarbon, e.g., isoprene ($C_5H_8$), and oxygen ($O_2$) content of the gaseous headspace with $CO_2$, and passage through a cooled condenser and through a hydrophobic solvent enables trapping and retention of the volatile hydrocarbon while effecting separation of the volatile hydrocarbon from the $O_2$ by-product of photosynthesis. In some embodiments, the volatile hydrocarbon is isoprene. In some embodiments, the photosynthetic organisms, e.g., microalgae or cyanobacteria, are genetically engineered, e.g., by introducing a heterologous isoprene synthase gene into the organism, to produce isoprene.

The methods of the present invention also include sequestration of isoprene and subsequent trapping in alcohol- or hydrocarbon-based solvents to form stable blends; these are also described. The invention can be employed with a fed-batch or a continuous culturing system.

The diffusion-based process in gaseous/aqueous two-phase photobioreactors governing the exchange of $CO_2$ with a volatile product of photosynthesis and leading to the generation, sequestration and trapping of industrially important molecules can be applied to other photosynthetically derived volatile compounds emanating from a variety of photosynthetic microorganisms at industrial scale. For example, and in addition to isoprene, these include, but are not limited to, volatile alcohols such as ethanol, butanol and isobutanol; and aldehydes such as acetaldehyde, butyraldehyde and isobutyraldehyde.

The following explanations of terms and methods are provided to better describe the present disclosure and to guide those of ordinary skill in the art in the practice of the present disclosure.

As used herein "a" or "an" or "the" include plural references unless the context clearly dictates otherwise.

The term "volatile hydrocarbon" typically refers to a compound that is composed of hydrogen and carbon atoms organized in linear or branched molecules. For purposes of this application, the term is also employed to encompass certain alcohols and aldehydes. Thus, as used herein, "volatile hydrocarbon" refers to short chain hydrocarbon molecules that have a boiling point at atmospheric pressure of less than 100° C. Examples of such hydrocarbon molecules include isoprene. In the context of this invention, the term also encompasses short chain alcohols and aldehydes that have a boiling point at atmospheric press pressure of less than 100° C. Examples of such alcohols are ethanol, butanol, and isobutanol. Examples of such acetaldehydes are butyraldehyde and isobutyraldehyde.

The term "volatile isoprene hydrocarbon" as used herein refers to a 5-carbon, short chain isoprenoid, e.g., isoprene or methyl-butenol.

Bioreactor Configurations.

The term "photobioreactor" as used herein refers to a bioreactor that provides for a light source to deliver photonic energy input into the reactor. The term in the context of this invention typically refers to a system that is substantially closed to the environment and has no direct exchange of gases and contaminants with the environment. A photobioreactor can be described as an enclosed, illuminated culture vessel designed for controlled biomass production of phototrophic liquid cell suspension cultures. Although the following examples may use isoprene to illustrate the invention, one of skill in the art understands that other volatile products of photosynthesis may be obtained using the same methods.

Figure 10:
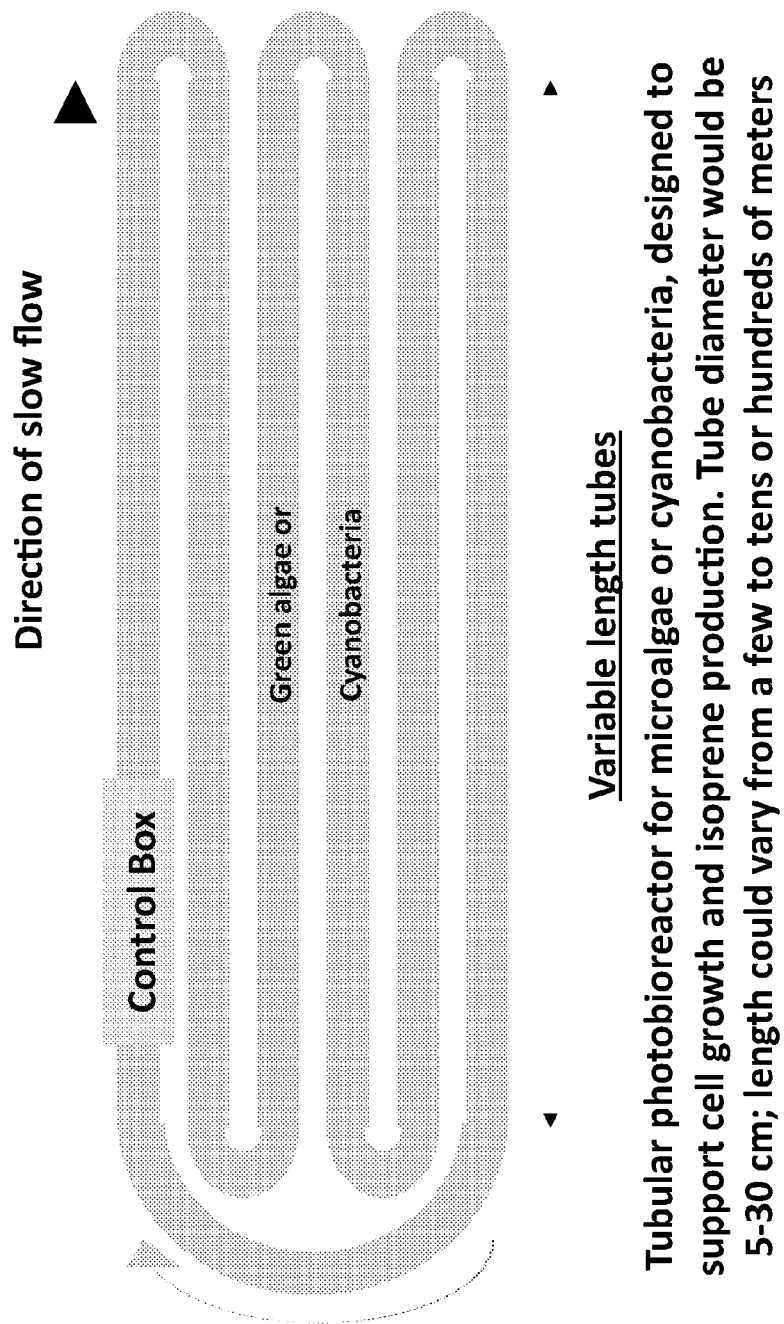
FIG. 10. Top view of illustrative tubular modular photobioreactor layout. Tubular modular photobioreactors for microalgae or cyanobacteria are designed to support cell growth and isoprene production. Tube diameter can be, e.g., 5-30 cm; Length can vary, e.g., from a few to tens or hundreds of meters.
Figure 11:
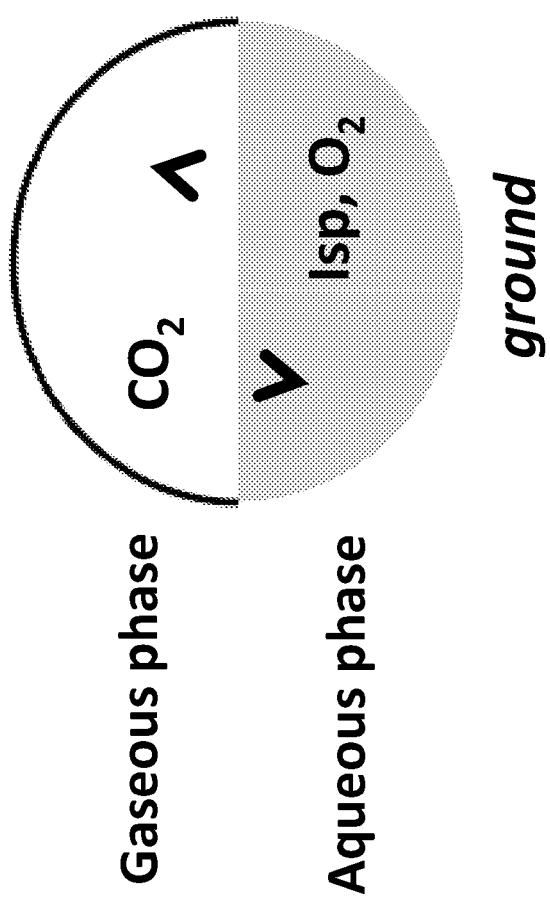
FIG. 11. Cross sectional view of illustrative photo-bioreactor tube, showing the gaseous/aqueous two-phase partition. The schematic shown depicts a 50:50 partition between the gaseous and aqueous phases. However, the gaseous/aqueous partition ratio could vary, e.g., between 1:9 and 9:1 values.

There are many different configurations of photobioreactor known in the art that can be employed in this invention. For example, although a tubular horizontal photobioreactor is offered as an illustrative example (FIGS. 10 and 11), it is understood that the invention described herein can be applied equally well with tubular vertical photobioreactors (e.g., principle of FIG. 1), as well as with photobioreactors having a variety of geometries, inclinations and shapes, including but not limited to tubular square, tubular oval or ellipsoid, tubular rectangular, flat panel, bubble column, air-lift, stirred tank, lake model, and immobilized substrate photobioreactors, among others. Tubular photobioreactors are examples of a design suitable for microalgae or cyanobacteria cultivation, designed to support cell growth and isoprene production. The tube structure can be made from a variety of materials ranging from polyethylene to plexiglass and glass. Tube diameter and length can vary, e.g., depending on the size of the bioreactor. For example, the diameter may vary from about 5-30 cm and the length can vary from a few to tens or hundreds of meters in length. On the basis of the modular bioreactor schematic shown in FIG. 10, a tube diameter of 15 cm translates into a 450 L total capacity reactor volume. If the tube diameter of the bioreactor is 30 cm, then the total internal volume of the reactor is 3,500 L. Those skilled in the art understand that far greater capacity reactor volumes can be attained with 5-30 cm diameter reactors upon increasing the overall length of the tubes. The operator pumps aqueous media, e.g., water suitably fertilized and properly inoculated with the microalgae, to fill the space assigned to the aqueous portion of the reactor (FIG. 11). The remainder of the reactor space is filled with $CO_2$, for example, 100% $CO_2$, or a $CO_2$ mix where the mix is at least 10% $CO_2$, at least 20% $CO_2$, at least 30% $CO_2$, at least 40% $CO_2$, preferably greater than 50% $CO_2$, e.g., at least 60% $CO_2$, at least 70% $CO_2$, at least 80% $CO_2$, or at least 90% or at least 95%, or greater, $CO_2$, to support the growth of the photosynthetic microorganisms. In embodiments in which the $CO_2$ is less than 100%, the remainder of the gaseous mixture is air. For example, FIG. 11 shows a cross-sectional view of a photobioreactor tube, showing the gaseous/aqueous two-phase partition. The schematic shown depicts a 50:50 partition between the gaseous and aqueous phases. However, the gaseous/aqueous partition ratio can vary considerably, e.g., can be in the range of about 1:9 to about 9:1. In some embodiments, the ratio is in the range of from about 4:6 to about 6:4.

Typical bioreactor assemblies for use in the invention include a port/valve for the introduction of $CO_2$ and a separate port/valve through which the $O_2$/volatile hydrocarbons, e.g., isoprene-containing gas, is removed. In typical embodiments, the methods of the invention avoid continuous bubbling and rely on periodically filling of the gaseous head space with $CO_2$ and then maintaining the head space of the photobioreactor in a resting stage, i.e., $CO_2$ is not continuously introduced, mixed, or bubbled, and relying on diffusion-driven uptake of $CO_2$ from the gaseous phase into the liquid phase to become available to the photosynthesizing microorganisms.

Carbon dioxide replacement and volatile hydrocarbon, e.g., isoprene, removal from the gaseous headspace of the photo-bioreactor takes place periodically, for example, every 3 hours, every 6 hours, every 18 hours, every 24 hours, or every 48 hours, or at longer periods of time, depending on the photosynthetic productivity of the cells. The following illustration refers to isoprene, but also applies to other volatile hydrocarbons known in the art and as described herein. For example, when sunlight is the light source, on sunny summer days $CO_2$ replacement and isoprene removal from the gaseous headspace of the photo-bioreactor is typically performed every 24 hours. On overcast and low-sunlight-intensity days, $CO_2$ replacement and isoprene removal occurs at longer periods of time.

In vertical tubular photobioreactors, $CO_2$-rich gases are typically slowly bubbled at the bottom of the liquid phase, as illustrated by example in FIG. 1. In horizontal tubular photobioreactors, $CO_2$-rich gases are applied either by bubbling the liquid phase, or applied as a stream of gas over the surface of the liquid phase. In either case, care is taken to ensure that fresh $CO_2$ gas is applied from a valve located at one end of the "control box" in the photobioreactor assembly, whereas gaseous products of photosynthesis and volatile hydrocarbon, e.g., isoprene, removal takes place at the other end of the control box from a separate valve. This can be effectively achieved, e.g., by introducing a retractable divider in the middle of the "Control Box" (FIG. 10) such that the port/valve for the application of the $CO_2$ is separated from the port/valve for the removal of the volatile hydrocarbon, e.g., isoprene, and $O_2$ products of photosynthesis. This approach ensures that a stream of $CO_2$ gas flows from one end of the control box through the entire length of the bioreactor tube before arriving at and exiting from the other end of the control box. In such an embodiment, the turbulence generated by the flowing stream of $CO_2$ in the gaseous phase of the reactor pushes out and removes the products of photosynthesis (volatile hydrocarbon, e.g., isoprene and $O_2$). Alternatively, in some embodiments, the gaseous products of photosynthesis can be removed in a similar manner by using a stream of air to purge the products of photosynthesis, which then is followed by filling the gaseous head phase of the reactor with $CO_2$ for further photosynthesis and production.

The volatile hydrocarbon, e.g., isoprene, is harvested by passing the gaseous phase that contains the volatile hydrocarbon, e.g., isoprene, and $O_2$ through a cooled condenser. The volatile hydrocarbon, e.g., isoprene, may then be collected. In some embodiments, the condensed hydrocarbon, e.g., condensed isoprene, is passed through a solvent, typically an organic solvent. Alcohols such as methanol (boiling point 64.7° C.), ethanol (boiling point 78.0° C.), butanol (boiling point 117.7° C.), and pure hydrocarbons such as hexane (boiling point 69.0° C.), heptane (boiling point 98.4° C.), octane (boiling point 125.5° C.), and dodecane (boiling point 216.2° C.) readily form stable "blends" with isoprene, or other volatile hydrocarbons obtained in accordance with the invention, thereby facilitating its retention and stabilization in a liquid solution. Concentrations of isoprene (or, e.g., alcohol, aldehyde, or other volatile hydrocarbon) collected in this manner vary between 1%, when a solvent is used to trap the isoprene, and 100% isoprene when no solvent is used, but a condenser-temperature low enough is employed to enable retention of isoprene in the liquid phase.

Examples of photobioreactors include cylindrical or tubular bioreactors, see, e.g., U.S. Pat. Nos. 5,958,761, 6,083,740, US Patent Application Publication No. 2007/0048859; WO 2007/011343, and WO2007/098150. High density photobioreactors are described in, for example, Lee, et al., *Biotech. Bioengineering* 44: 1 161-1 167, 1994. Other photobioreactors suitable for use in the invention are described, e.g., in WO/2011/034567 and references cited in the background section. Photobioreactor parameters that can be optimized, automated and regulated for production of photosynthetic organisms are further described in (Puiz (2001) *Appl Microbiol Biotechnol* 57:287-293). Such parameters include, but are not limited to, materials of construction, efficient light incidence into reactor lumen, light path, layer thickness, oxygen released, salinity and nutrients, pH, temperature, turbulence, optical density, and the like.

Examples of light sources that are used to provide the energy required to sustain photosynthesis include, for example, fluorescent bulbs, incandescent light, LEDs, and natural sunlight.

Aqueous Phase

The aqueous phase contains a medium that supports growth of the photosynthetic microorganism. The microorganism can be cultivated using various cultivation techniques, include continuous and fed-batch cultivation methods.

Photosynthetic microorganisms that are cultured in the photobioreactors include cyanobacteria and green microalgae. The microorganisms may grow in fresh or salt water. Examples of microorganisms that can be cultured in accordance with the invention include cyanobacteria (e.g., *Nostoc, Anahaena, Spirulina, Synechococcus, Synechocystis, Athrospira, Gleocapsa, Oscillatoria*, and *Pseudoanabaena*). In some embodiments the algae is a microalga (e.g., *Chlamydomonas reinhardtii*, or other member of the genus *Chlamydomonas;* a member of the genus *Dunaliella*, or a member of the genus *Chlorella*. In some embodiments, the algae is a green algae, for example algae from the genus *Tetraselmis*, the genus *Micractinium*, the genus *Desmodesmus*, the genus *Scenedesmus*, the genus *Nannochloropsis* or the genus *Botryococcus*.

In typical embodiments, the microorganism, e.g., cyanobacteria or green microalgae is engineered to express a heterologous gene encoding an isoprene synthase, or other enzyme that generates isoprene or other volatile compounds. In some embodiments, the genetically engineered photosynthetic microorganism produces a volatile isoprenoid hydrocarbon from precursors generated via the 2-C-methyl-D-erythritol-4-phosphate (MEP) metabolic pathway and/or the mevalonate pathway. A wide variety of cyanobacteria and green algae can be engineered to express an isoprene synthase. These include *Chlamydomonas reinhardtii, Scenedesmus obliquus, Chlorella vulgaris, Botryococcus braunii, Botryococcus sudeticus, Dunaliella salina*, and *Haematococcus pluvialis*. Cyanobacteria that can be genetically modified include thermophilic cyanobacteria, such as *Thermosynechococcus elongatus*; and cyanobacteria of the genera *Synechococcus, Synechocystis* and *Anabaena*, including the species *Synechocystis* sp. PCC 6803 and *Anabaena* 7120. Genetically modified cyanobacteria, green microalgae and other microorganisms and methods of producing isoprene using such genetically modified cyanobacteria are described, e.g., in WO/2008/003078 and WO2008/137092.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

Continuous Cultivation

In some embodiments, the methods of the invention employ a continuous culturing system to maintain cultures in a constant state of exponential growth. In such embodiments, cultures are fed periodically with $CO_2$, e.g., every 24 to 48 hours, to support high photoautotrophic growth rates. In addition, cultures are periodically diluted with fresh growth medium, e.g., every 24 to 48 hours. In some embodiments when cultures reach a density of about 0.7 g dw $L^{-1}$ or greater, cultures are diluted to a density of about 0.05 to about 0.6 g dw $L^{-1}$, typically to a density of about 0.1 to about 0.4 g dw $L^{-1}$, for example to about 0.1 g dw $L^{-1}$, about 0.2 g dw $L^{-1}$, about 0.3 g dw $L^{-1}$, or about 0.4 g dw $L^{-1}$.

Fed-Batch

A fed-batch is a batch process of growth, which is based on providing finite amounts of a nutrient substrate to a culture of microalgae or cyanobacteria. The principle applies equally well to fermentative organisms such as yeast or bacteria. The fed-batch strategy is to reach a high cell density in the photobioreactor. The growth medium is designed to be optimal for the fast growth of the microorganism, without causing deleterious side effects. At the end of the growth period, the products are then harvested.

EXAMPLES

Example 1

Obtaining Isoprene from Cyanobacteria that Express Heterologous Isoprene Synthase Strains and Growth Conditions The glucose-tolerant cyanobacterial strain *Synechocystis* sp. PCC 6803 (Williams, 1988) was used as the recipient strain in this study, and is referred to as the wild type. The codon-optimized isoprene synthase gene from *Pueraria montana* (the kudzu vine IspS gene) was employed for the transformation of the wild type (Lindberg et al., 2010). The heterologous transformed cyanobacteria are referred to as SkIspS transformants. Wild type and SkIspS transformant strains were maintained on solid BG-11 media supplemented with 10 mM TES-NaOH (pH 8.2), 0.3% sodium thiosulfate, and 5 mM glucose. Where appropriate, kanamycin was added at a concentration of 5 µg/mL. Liquid cultures, including those used for aerated photoautotrophic growth experiments, were grown in BG-11 containing 25 mM HEPES-NaOH, pH 7.5. Liquid cultures for inoculum purposes were maintained at 25° C. under a slow stream of constant aeration and illumination at 20 µmol photons $m^{-2}s^{-1}$.

Generation of *Synechocystis* Transformants with Heterologous Expression of the IspS Gene Wild-type *Synechocystis* sp. PCC 6803 was transformed with the plasmid construct pBA2SkIKmA2, which was earlier described by Lindberg et al. (2010). This plasmid facilitates the replacement of the *Synechocystis* PsbA2 gene with the *Synechocystis* codon optimized kudzu IspS (SkIspS) gene via double homologous recombination. The SkIspS transformants described in this work differ from the SkIspS transformant by Lindberg et al. (2010) only in terms of the wild-type genetic background. (The SkIspS transformants by Lindberg et al. was generated from the glucose-sensitive *Synechocystis* sp. PCC 6803 strain.) Transformations were carried out according to established procedures (Williams, 1988; Eaton-Rye, 2004). The successful transgene incorporation and complete DNA cyanobacterial copy segregation for the SkIspS gene was verified by genomic DNA PCR, using primers designed within the upstream and downstream regions of the PsbA2 gene that were used for homologous recombination.

Chlorophyll Determination, Photosynthetic Productivity and Biomass Quantitation

Chlorophyll a concentrations in cultures were determined spectrophotometrically in 90% methanol extracts of the cells according to Meeks and Castenholz (1971). Photosynthetic productivity of the cultures was tested polarographically with a Clark-type oxygen electrode (Rank Brothers, Cambridge, England). Cells were harvested at mid-exponential growth phase, and maintained at 25° C. in BG11 containing 25 mM HEPES-NaOH, pH 7.5, at a chlorophyll a concentration of 10 µg/mL. Oxygen evolution was measured at 25° C. in the electrode upon yellow actinic illumination, which was defined by a CS 3-69 long wavelength pass cutoff filter (Corning, Corning, N.Y.). Photosynthetic activity of a 5 mL aliquot of culture was measured at varying actinic light intensities in the presence of 15 mM $NaHCO_3$, pH 7.4, to generate the light saturation curve of photosynthesis. Culture biomass accumulation was measured gravimetrically as dry cell weight, where 5 mL samples of culture were filtered through 0.22 µm Millipore filters and the immobilized cells dried at 90° C. for 6 h prior to weighing the dry cell weight.

Diffusion-Based Growth in Fed-Batch or Continuous Growth Gaseous/Aqueous Two-Phase Bioreactors One-liter fed-batch bioreactors for laboratory-scale work were designed by us and custom-made (Adams and Chittenden Scientific Glass, Berkeley, Calif.) from 1 L Corning Pyrex bottles that were modified to have two sidearm openings (FIG. 1). A long aerator tube was fixed within one side arm to enable delivery of gasses (different concentrations of $CO_2$ or air), which were slowly bubbled though the bottom of the liquid medium. All gasses provided to the culture were first passed though a 0.2 µm filter unit (Millex-FG Filter Unit, Millipore) to maintain sterility. The second side arm functioned as a headspace sampling and/or photoproduct removal tube, from which headspace gasses (isoprene and $O_2$) were vacated and replaced with fresh $CO_2$ for extended photosynthesis, growth, and productivity. Alternatively, the headspace sampling/product removal tube could also be used for liquid culture sampling through a septum. Both side arms were fitted with stopcocks so that the headspace of the bioreactor could be sealed. In continuous growth bioreactors, a drain tap was installed near the bottom of the vessel that enabled a regulated removal of aliquots of the culture (not shown).

Bioreactors were seeded with 700 mL culture (about 60% volume of the 1 L bioreactor) and *Synechocystis* cells at an $OD_{730}$ of 0.05 in BG11 medium, containing 25 mM HEPES-NaOH, pH 7.5, and grown under continuous illumination at 75 μmol photon $m^{-2}s^{-1}$ until an $OD_{730}$ of approximately 0.5 was reached. Inorganic carbon delivery to the culture was made in the form of 500 mL aliquots of 100% $CO_2$ gas, slowly aerated through the bottom of the liquid culture and into the bioreactor headspace (FIG. 1). As $CO_2$ gas is heavier than $N_2$ and $O_2$, slow bubbling was necessary and sufficient to purge $N_2$ and $O_2$ from the headspace through the sampling/product removal tube, and to replace them with $CO_2$ in the headspace. Once atmospheric gases were replaced with 100% $CO_2$ in the headspace, the bioreactor was sealed and the culture was incubated upon illumination at 150 μmol photons $m^{-2}s^{-1}$ and 35° C., conditions that promoted $CO_2$ uptake from the gaseous headspace and photosynthetic assimilation of the $CO_2$, leading to biomass and isoprene production. It was determined that cells in the liquid growth medium efficiently took-up via diffusion $CO_2$ from the headspace, replacing it with isoprene vapor and $O_2$ as products of photosynthesis. Such diffusion-based method for gas exchange and isoprene production by photosynthetic microorganisms alleviates the need of continuous bubbling of cultures, while permitting for product (isoprene) accumulation and sequestration in the headspace. It was determined that high rates of photosynthesis, growth and productivity could thus be supported by this method (please see below). Periodically, as required by the culture growth and productivity conditions, $CO_2$ gas bubbling through the culture was repeated to recharge the $CO_2$ supply in the headspace of the culture and to remove the isoprene and $O_2$ products of photosynthesis from the reactor.

For continuous growth and productivity experiments, daily $CO_2$ flushes were administered to the culture as described above and, after every 48 hours of $CO_2$ diffusion-supported growth, cultures were diluted with fresh growth medium, down to an $OD_{730}$ of 0.5 (dry cell weight of ~0.2 g $L^{-1}$), to ensure cells were always in the exponential phase of growth.

Isoprene Production Assays

Figure 2:
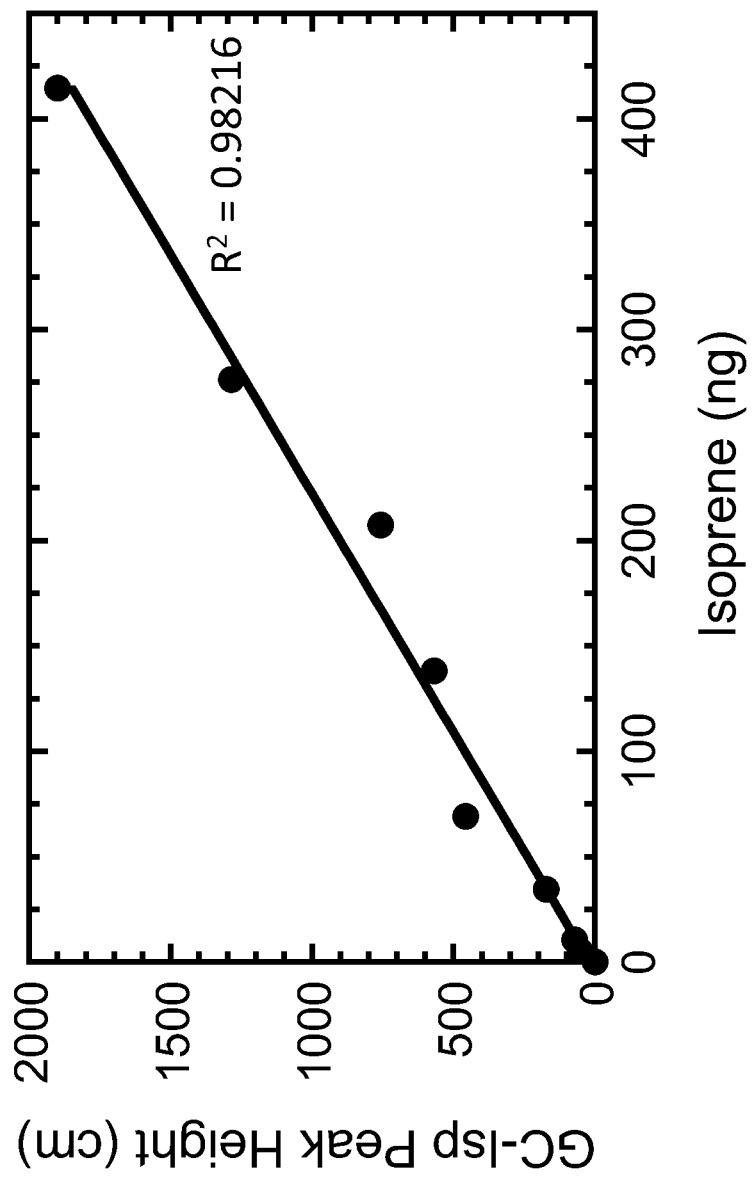
FIG. 2 shows an example of a calibration curve plotting the isoprene peak height of a gas chromatography (GC) readout as a function of isoprene amount injected in the GC. A serial dilution of vaporized pure isoprene standard of known concentrations was employed. A 1 mL sample of each standard was injected and analysed by the GC. The calibration curve was based on the amount of isoprene (ng) in the 1 mL sample relative to the isoprene peak height from the chromatogram. At higher isoprene concentrations, the GC sensitivity was attenuated to enable the measurement of the large amplitude peaks, and this attenuation was corrected for in the presentation of the calibration curve.

Gas from the headspace of sealed bioreactors was periodically sampled and analyzed by gas chromatography using a Shimazu 8A GC (Shimazu, Columbia, Md., USA) equipped with a flame ionization detector (FID) and a column appropriate for detection of short-chain hydrocarbons. Quantitation of isoprene production was performed on the basis of an isoprene vapor calibration curve (FIG. 2) constructed by the GC analysis of a series dilution of a vaporized pure isoprene standard (Acros Organics, Fair Lawn, N.J., USA).

Example 2

Figure 3:
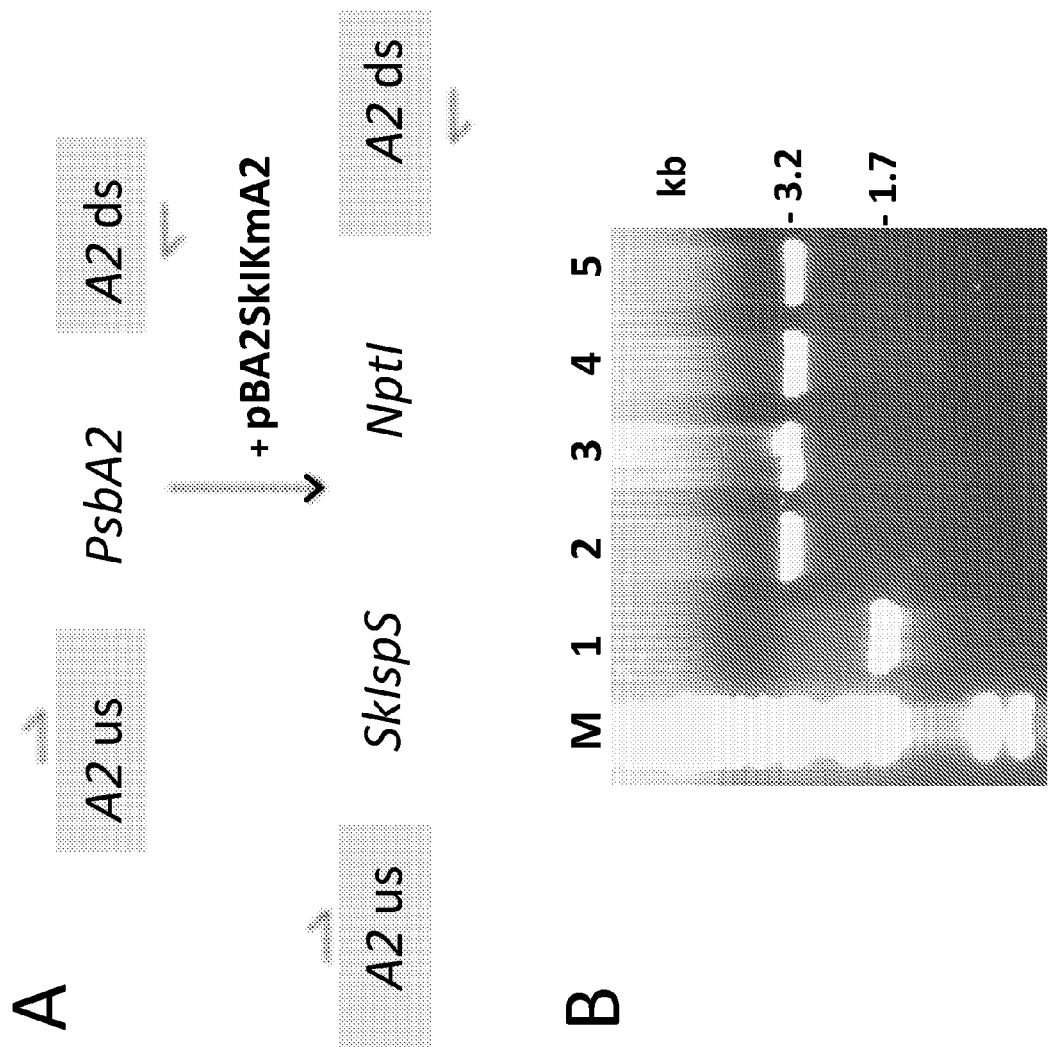
FIG. 3 provides an example of data for double homologous recombination and *Synechocystis* DNA copy segregation in expressing an IspS gene. A. Maps of the PsbA2 gene locus in wild-type *Synechocystis* and of the SkIspS-NptI gene construct for double homologous recombination. Cells were transformed with plasmid pBA2SkIKmA2 (Lindberg et al., 2010) designed to replace the endogenous PsbA2 with a heterologous SkIspS gene and a kanamycin antibiotic selectable NptI marker. Genomic PCR primers (arrows) to the upstream and downstream regions of the PsbA2 gene (A2us, A2ds) were designed to amplify a 3.188 kb product in the SkIspS transformant compared to a 1.717 kb in the wild type. B. A PCR product of ~1.7 kb was amplified in the wild type containing the endogenous PsbA2 (lane 1), whereas larger products of ~3.2 kb were amplified in four independent SkIspS transformant lines (lanes 2-5). Absence of the 1.7 kb product from the latter shows DNA copy segregation in the transformants following the replacement of PsbA2 with the heterologous SkIspS transgene construct. M, 1 kb plus marker.

Diffusion-Based $CO_2$ Uptake Assimilation and Isoprene Production in Gaseous/Aqueous Two-Phase Photobioreactors by Photosynthetic Cyanobacteria Transformation, DNA Copy Homoplasmy, and IspS Transgene Expression Substitution of the PsbA2 gene with the *Synechocystis* codon-optimized kudzu IspS gene construct (SkIspS) was implemented by double homologous recombination (FIG. 3A), as previously described (Lindberg et al., 2010). *Synechocystis* has multiple copies of its circular DNA in the cell, all of which would need to contain the IspS transgene. Achieving such "homoplasmy" among the *Synechocystis* DNA copies is essential for further cultivation and isoprene production in the absence of the selectable marker (kanamycin). Segregation of the *Synechocystis* DNA copies (homoplasmy) was achieved upon cultivation of the transformants for several generations under antibiotic selective pressure, which promoted deletion of wild type copies of the *Synechocystis* DNA and replacement with the IspS transgene-containing copy.

DNA copy homoplasmy was tested by the absence of wild-type copies of the PsbA2 locus in four randomly selected transformant lines. Genomic DNA PCR analysis was undertaken with primers designed to the upstream and downstream regions of PsbA2 gene. These would amplify a larger product in the transformant than in the wild type, corresponding to the replacement of the endogenous 1083 by PsbA2 with the larger 1718 by SkIspS gene fused to a 836 by NptI kanamycin-resistance cassette. Indeed, wild-type DNA amplified a single PCR product of about 1.7 kb (FIG. 3B, lane 1), corresponding to the wild-type PsbA2 locus. In four randomly selected transformants (FIG. 3B, lanes 2-5) genomic DNA PCR also showed a single PCR product of about 3.2 kb, corresponding to the transgene-containing PsbA2 locus. Absence of wild-type size products from the latter is evidence of complete segregation of the *Synechocystis* DNA copies, all of which now contain the introduced SkIspS transgene.

Figure 4:
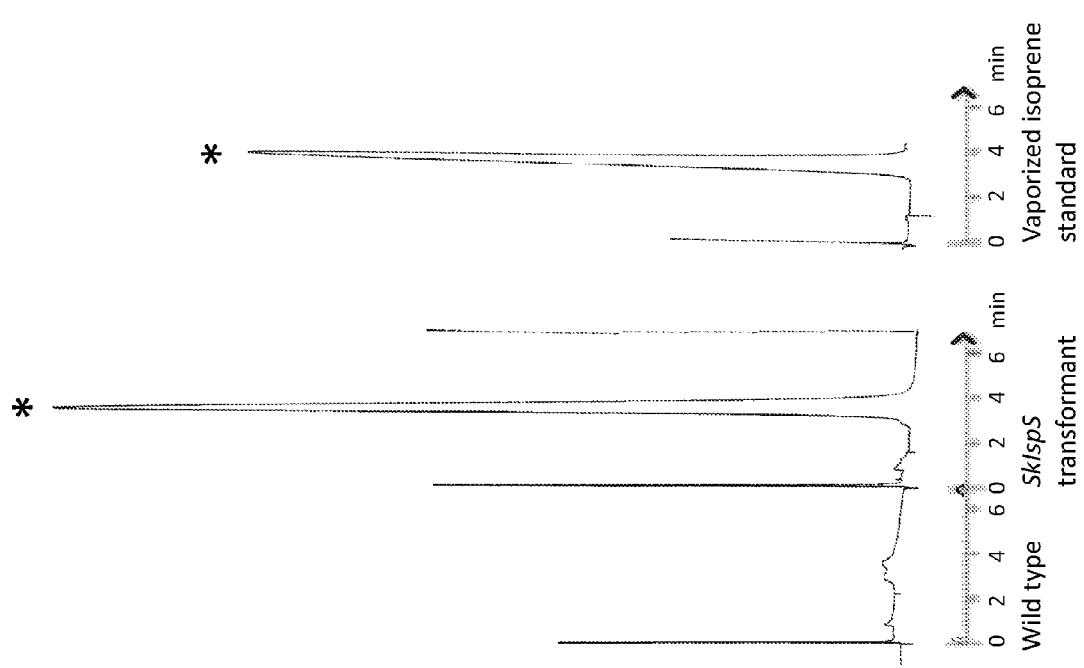
FIG. 4 shows an example of a GC analysis of gases in the headspace of wild-type and SkIspS transformant cultures. Cultures were sealed for 48 h in the presence of $CO_2$. GC analysis of headspace gases from wild type (left panel) and the SkIspS transformant (middle panel). Isoprene peaks were identified by comparison with an isoprene vapor standard (right panel), and are labeled with asterisks.

Cultivation of wild type and SkIspS transformants under conditions of the gaseous/aqueous two-phase bioreactor described in FIG. 1 tested for the production and accumulation/sequestration of isoprene hydrocarbons in the culture headspace. In this experiment, the gaseous headspace of the bioreactor was filled with 100% $CO_2$, followed by sealing of the culture and incubation under photosynthesis conditions for 48 h. Analysis of the accumulated reactor headspace gases in the wild type showed no evidence of isoprene hydrocarbons (FIG. 4, left panel). The headspace of the SkIspS transformant showed substantial isoprene accumulation, as evidenced by the GC peak with a 3.5 min retention time (FIG. 4, middle panel). Isoprene was the sole short-chain volatile hydrocarbon generated by photosynthesis in the transformant (compare with the isoprene standard shown in FIG. 4, right panel). These results are evidence that the SkIspS transgene and its encoded isoprene synthase enzyme are responsible for the catalysis of isoprene production in the transformant strains.

Growth and Photosynthesis of *Synechocystis* Wild Type and SkIspS Transformants

Figure 5:
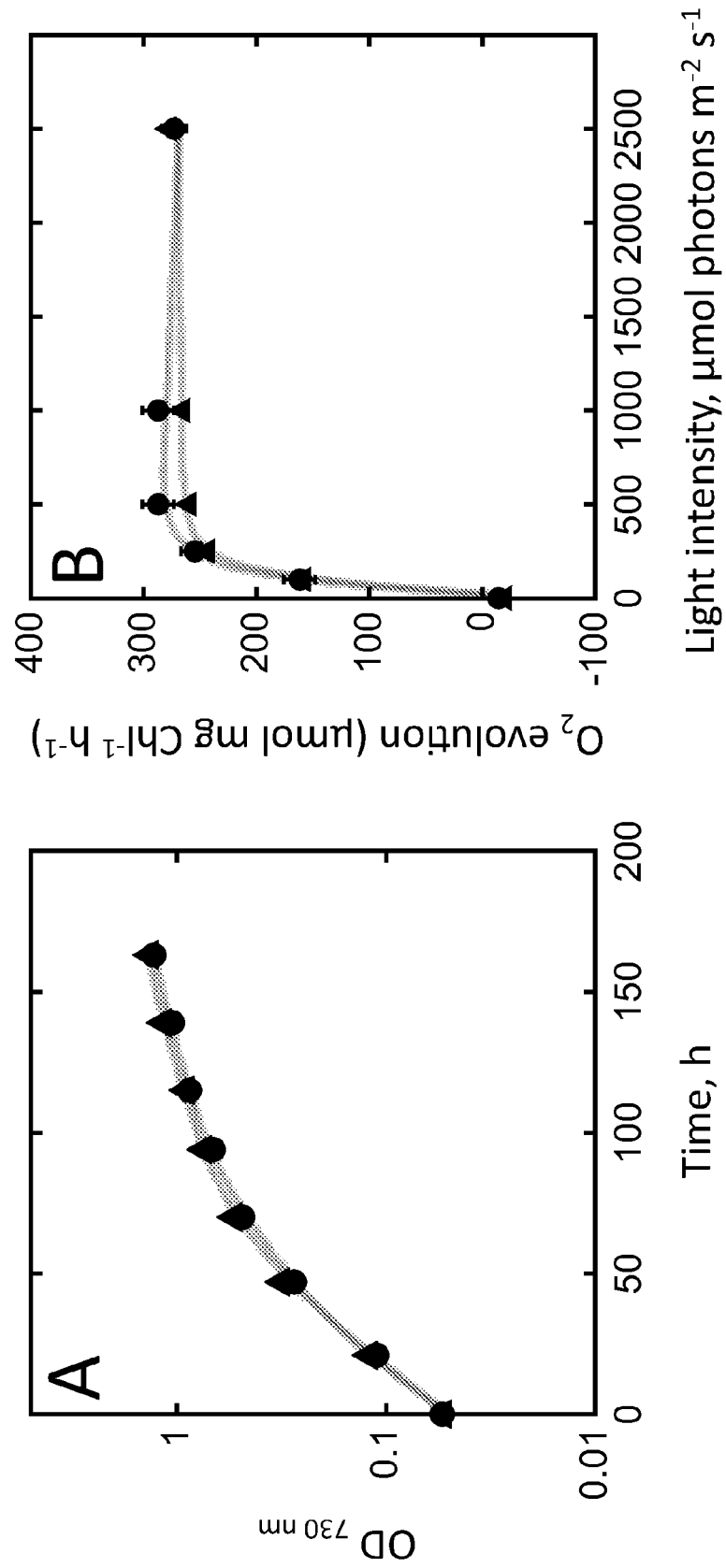
FIG. 5 provides examples of data showing the growth and photosynthesis of wild type and SkIspS transformants in liquid culture. A. Photoautotrophic growth kinetics of wild-type (triangles) and SkIspS transformant cells (circles), as measured by optical density at 730 nm, when grown with continuous aeration and continuous illumination at 20 µmol photons $m^{-2}s^{-1}$. B. Light saturation curves of photosynthesis for wild type and SkIspS transformant cells, as measured by the oxygen-evolution activity of an aliquot of the cultures in the presence of 15 mM $NaHCO_3$, pH 7.4 under a range of actinic light intensities.

The photoautotrophic cell growth kinetics of the SkIspS transformants were about the same as that of the wild type, with a doubling time of 23 h under a light intensity of 20 μmol photons $m^{-2}s^{-1}$ (FIG. 5A). The light saturation curves of photosynthesis of wild type and the SkIspS transformants were also similar to one another (FIG. 5B), where oxygen evolution saturated at about 500 μmol photons $m^{-2}s^{-1}$, with an average $P_{max}$ of 263 μmol $O_2$ (mg Chl)$^{-1}$ h$^{-1}$ in wild type and 287 μmol $O_2$ (mg Chl)$^{-1}$h$^{-1}$ in the SkIspS transformant (FIG. 5B). Similarly, rates of oxygen consumption during dark respiration were about the same in the wild type and SkIspS transformants and equal to about −17 μmol $O_2$ (mg Chl)$^{-1}$h$^{-1}$. Importantly, at sub-saturating light intensities between 0 and 250 μmol photons $m^{-2}s^{-1}$, rates of oxygen evolution and the initial slopes of photosynthesis as a function of light intensity were comparable in wild-type and SkIspS-transformant cells (FIG. 5B), suggesting similar quantum yields of photosynthesis (Melis, 2009). These results (FIGS. 5A and 5B) clearly showed that deletion of the endogenous PsbA2 coding region from the *Synechocystis* genome, with the attendant replacement/integration and expression of the SkIspS transgene in the cell, as well as the subsequent generation and accumulation of isoprene, had no adverse effect on the growth and photosynthetic productivity parameters of the transformants.

Administration of a Single Dose of 100% $CO_2$

A 1-liter fed-batch bioreactor was employed, where a single 500 mL dose of 100% $CO_2$ was dispersed upon bubbling slowly through the 700 mL aqueous culture volume (FIG. 1). The $CO_2$ gas displaced other gases from the headspace of the 1 L bioreactor and, upon the subsequent sealing of the vessel, $CO_2$ was taken-up and assimilated in photosynthesis, leading to autotrophic biomass accumulation and isoprene production by *Synechocystis*. Exchange of $CO_2$ in the headspace for molecular oxygen and isoprene maintained equilibrium of gas pressure in the sealed headspace. When a single dose of 100% $CO_2$ was fed to cells at an $OD_{730\,nm}$ of 0.5 (FIG. 6A), cell growth and biomass accumulation was supported for ~48 h in both wild-type and SkIspS transformant cultures. This was evidenced by measurements of the $OD_{730\,nm}$ of the culture, which increased from 0.5 to about 2.5 in 48 h (FIG. 6A), increase in dry cell weight from 0.25 to about 0.7 g $L^{-1}$ (FIG. 6B), and increase in the chlorophyll content from 0.25 to about 0.75 mg $mL^{-1}$ culture (FIG. 6C). After about 48 h of growth, the $CO_2$ supply was depleted from the headspace and from the liquid medium of the culture, and cells entered the stationary phase of growth (FIG. 6A-C).

Isoprene concentration measurements from such fed-batch SkIspS cultures only (FIG. 6D) showed that a yield of over 100 mg isoprene $L^{-1}$ culture could be achieved from a single dose of $CO_2$. The initial rate of isoprene production was 2 µg isoprene $L^{-1}$ culture $h^{-1}$ and it occurred during the initial 48 h of exponential cell growth, with the rate of isoprene production slowing gradually as cells entered the stationary growth phase. Interestingly, isoprene accumulation continued well into the stationary phase of the culture, lasting for approximately 150 h after initiation of the $CO_2$ diffusion-based photoautotrophic growth process in the fed-batch bioreactor. This observation suggests that metabolic activity continues through the stationary phase of the cells and, although net biomass increase is no longer observed, nevertheless, internal cellular metabolism (possible the breakdown of cellular glycogen) suffices to sustain isoprene production for extended periods of time.

Sealing of the fed-batch bioreactors without prior feeding with $CO_2$ resulted in minimal biomass accumulation and isoprene production. Under these conditions, cells entered a photoinhibition state almost immediately upon sealing. Photoinhibition progressed into bleaching of the cells after about 48 h incubation under illumination conditions (results not shown).

Repetitive Administration of 100% $CO_2$ Dosage

Figure 7:
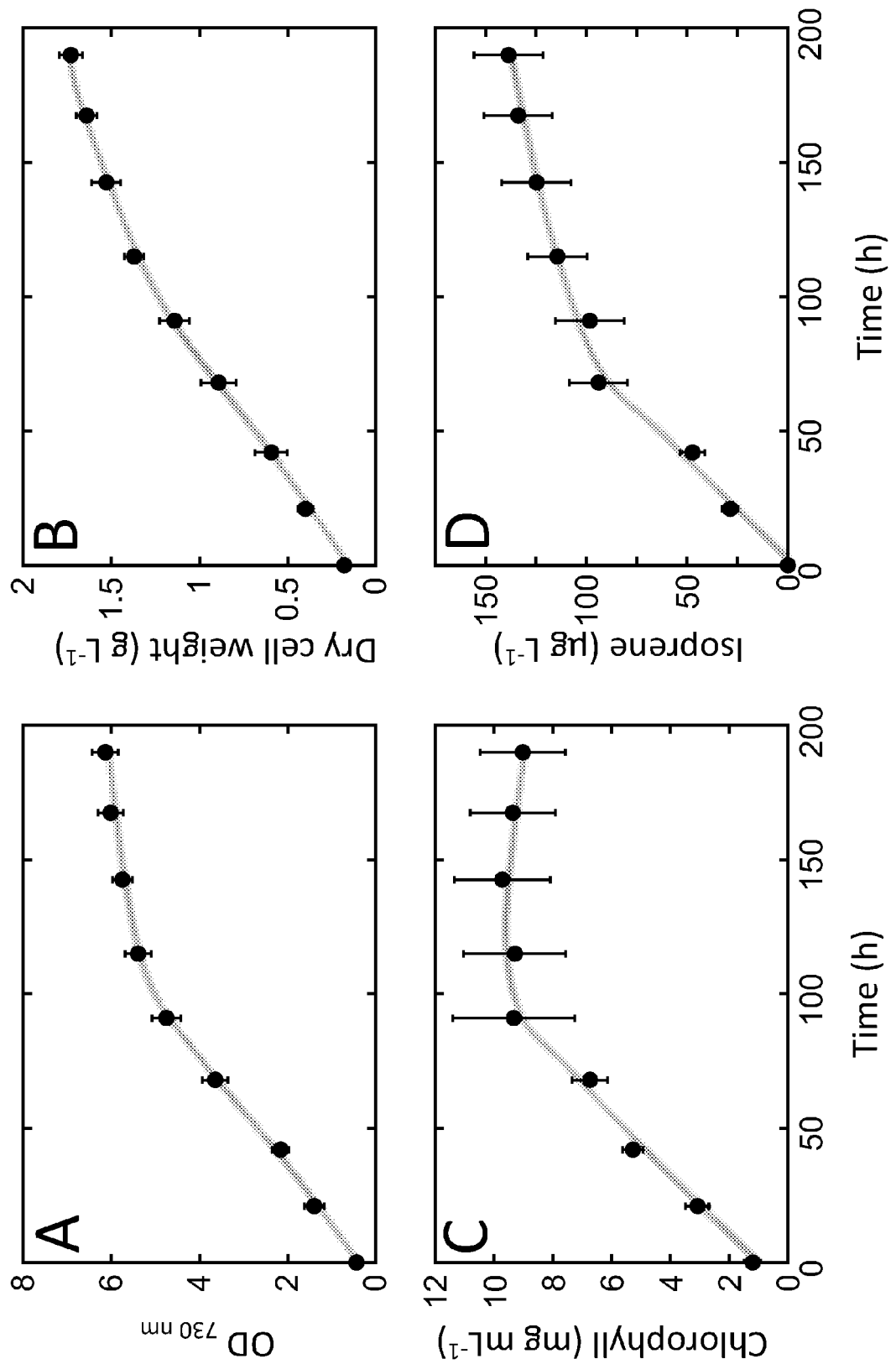
FIG. 7 provides examples of data showing cell growth and isoprene production upon periodic supplementation of $CO_2$ in a fed-batch gaseous/aqueous two-phase bioreactor. Cultures were bubbled slowly with 500 mL of 100% $CO_2$, sufficient to fill the headspace of the bioreactor upon displacement of other headspace gases. Supplementary doses with 500 mL of 100% $CO_2$ were administered approximately every 48 h, after which the headspace was sealed to allow $CO_2$ diffusion-based photoautotrophic growth and emission/accumulation of isoprene hydrocarbons. Each treatment of $CO_2$ effectively flushed all accumulated $O_2$ and isoprene vapor from the headspace. Accordingly, isoprene content was measured before and after flushing with $CO_2$ to yield an estimation of isoprene accumulation over each 24 h period. Over the time course of the experiment the following culture variables were measured: (A) cell density as $OD_{730\ nm}$, (B) dry cell weight, (C) chlorophyll concentration in the cultures, and (D) cumulative amount of isoprene produced per liter culture. Results are presented for the SkIspS transformant only and show the average of three independent experiments, for which error bars represent the standard deviation of the mean.

Entry into the stationary phase of growth at 48 h after the administration of a single dose of $CO_2$ was found to be due to the efficient diffusion-based uptake and assimilation of $CO_2$ from the culture headspace, leading to $CO_2$ depletion in the bioreactor. This interpretation was supported by the recovery of growth upon the repetitive administration of equivalent amounts of $CO_2$ into the reactor that invariably alleviated the growth inhibition. The results from such a repetitive administration of $CO_2$ are shown in FIG. 7. In this approach, a 500 mL dose of 100% $CO_2$ was administered every 48 h, while growth and productivity parameters were also measured. The $OD_{730\,nm}$ of the culture increased from 0.5 to about 6.5 in 192 h under these conditions (FIG. 7A). Also observed were increases in dry cell weight from 0.2 to about 1.8 g dw $L^{-1}$ (FIG. 7B) and in the chlorophyll content of the culture from 0.5 to about 10 mg $mL^{-1}$ (FIG. 7C). Isoprene concentration measurements from such fed-batch SkIspS cultures upon periodic supplementary administration of $CO_2$ (FIG. 7D) showed a yield of 150 mg isoprene $L^{-1}$ culture, and kinetics of isoprene accumulation that matched the kinetics of cell growth. Coupled with the extended exponential growth phase is a prolonged period of maximal isoprene production, where 100 µg isoprene $L^{-1}$ culture is achieved after only about 70 h of growth. The slower rate of biomass accumulation and isoprene production at times longer than 70 h in this experiment was a result of nutrient depletion in the media rather than a C-limitation, as growth in 2× concentration of nutrients sustained growth and isoprene production for a longer period of time (results not shown). However, rates of growth and isoprene production were not entirely improved under these nutrient-enhanced conditions, due to the high-density of pigments in the cultures, limiting irradiance penetration and utilization (Mita and Melis, 2008; 2010; Melis, 2009).

Continuous Growth for Biomass and Isoprene Production

Figure 6:
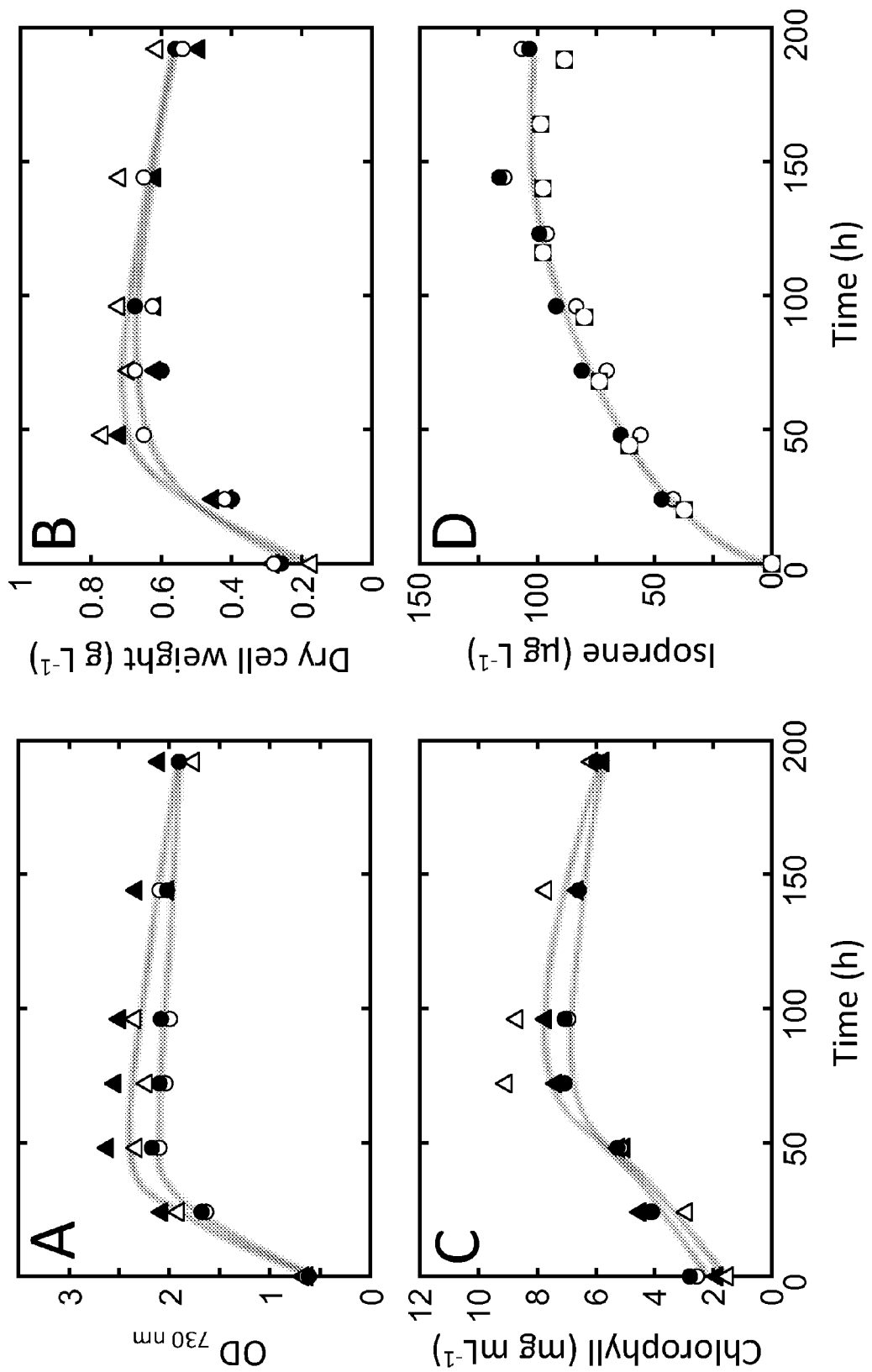
FIG. 6 provides examples of data showing $CO_2$ diffusion-supported photoautotrophic growth and isoprene production in a fed-batch bioreactor. Photoautotrophically grown cultures of *Synechocystis* (700 ml of liquid culture, which is equivalent to 60% of the bioreactor volume) were slowly bubbled with 500 mL of 100% $CO_2$ to fill the headspace of the culture upon displacement of other headspace gases. Measurements started with a culture $OD_{730\ nm}$=0.5. After administration of the 500 mL $CO_2$, the headspace of the gaseous/aqueous two-phase system was sealed and a time course of the following variables were undertaken: (A) cell density as OD730 nm, (B) dry cell weight, (C) chlorophyll concentration, and (D) amount of isoprene accumulated in the headspace per liter culture. Two independent measurements with separate samples are shown for each strain for cell density, dry cell weight and chlorophyll concentration. Three independent measurements are shown for isoprene accumulation with the SkIspS transformant. Wild type (triangles), SkIspS transformant (circles).
Figure 8:
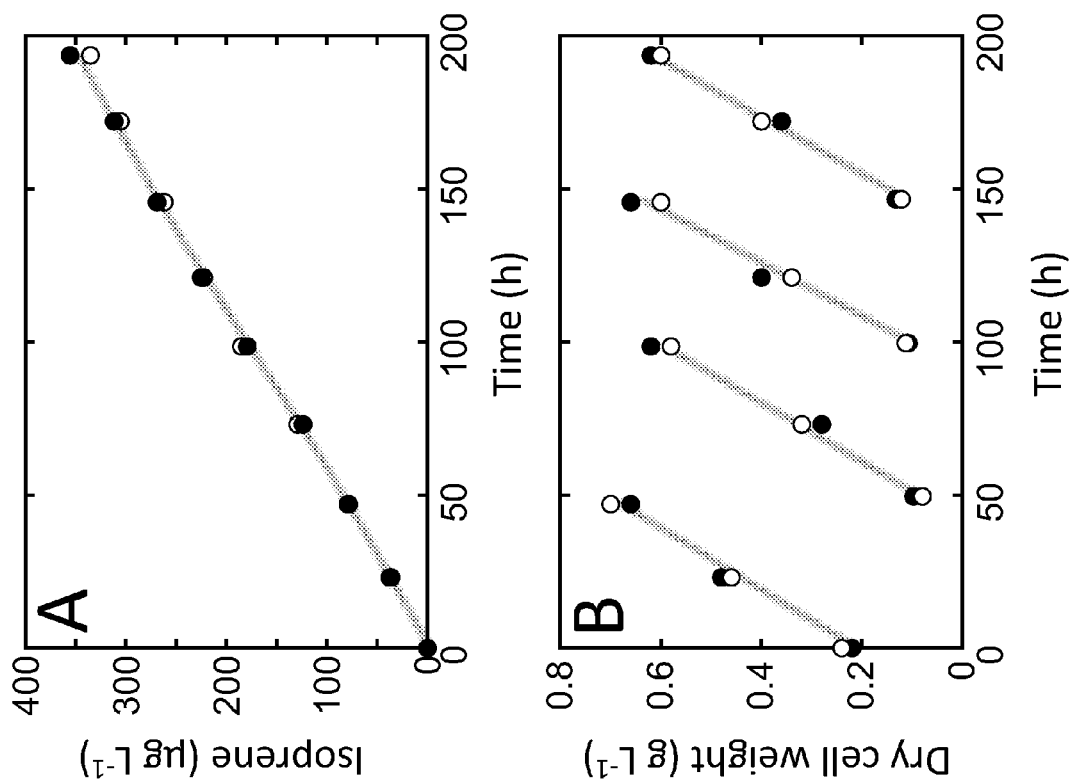
FIG. 8 provides an example of data showing continuous growth for biomass and isoprene production in an gaseous/aqueous two-phase bioreactor. SkIspS transformant cultures were administered 500 mL of 100% $CO_2$ approximately every 24 h to maintain photoautotrophic growth while the bioreactor was sealed for isoprene accumulation. Cultures were also diluted with fresh growth media every 48 h to an $OD_{730\ nm}$=0.5 (~0.2 g dw $L^{-1}$) in order to maintain cells in the exponential growth phase. (A) Isoprene hydrocarbons accumulated over the time course of the experiment. (B) Culture dry cell weight as a function of time during continuous growth in the bioreactor. Dilutions of the culture were implemented at 48, 96 and 144 h. Results shown are for two different SkIspS transformant lines.

The preceding experiments indicated that, under photoautotrophic growth conditions, maximum rates of isoprene accumulation were obtained when cell growth was maintained in a metabolically active state (FIGS. 6, 7). Therefore, a continuous culturing system was devised to maintain cultures in a constant state of exponential growth. Cultures were fed $CO_2$ every 24 h to support high photoautotrophic growth rates and, in addition, were diluted with fresh growth medium every 48 h, down to an $OD_{730\,nm}$ of 0.5 (~0.2 g dw $L^{-1}$). Using this approach, a constant rate of isoprene production of 2 µg isoprene $L^{-1}$ culture $h^{-1}$ was achieved over 192 h of experimentation (FIG. 8A). Over this period of time, three dilutions were administered, bringing the culture biomass density from about 0.7 g dw $L^{-1}$ prior to the dilution, to between 0.1-0.2 g dw $L^{-1}$ after the dilution with fresh growth media (FIG. 8B). It is evident from the results of FIG. 8 that both isoprene and biomass accumulation increased linearly with time after each dilution.

These results showed constitutive isoprene production under autotrophic culture conditions, in a process that is driven by photosynthesis in the cells. The excellent reproducibility of the results, the long duration of production, and the stability of the SkIspS transgenes in the transformant cyanobacteria provide methods and composition that can be applied under scale-up conditions, designed to support maximal rates of isoprene production over essentially an indefinite period of time.

Example 3

Example of Diffusion-Based $CO_2$ Uptake and Isoprene Production in Scale-Up Gaseous/Aqueous Two-Phase Photobioreactors Followed by Isoprene Trapping in Isoprene/Organic Solvent Blends Physicochemical Condensation and Capturing pf Isoprene Vapor from Mini-Scale-Up Cultures of Cyanobacteria and Green Microalgae Mini-scale-up experiments were conducted with 12 L and 20 L reactors in which the diffusion-based process of $CO_2$ uptake from the gaseous phase, assimilation and exchange with isoprene and $O_2$ from the photosynthesis in the aqueous phase permitted accumulation of greater relative amounts of isoprene. Separation of the isoprene hydrocarbons from $O_2$ was achieved via the application of a physicochemical method for the condensation and trapping of isoprene.

Figure 9:
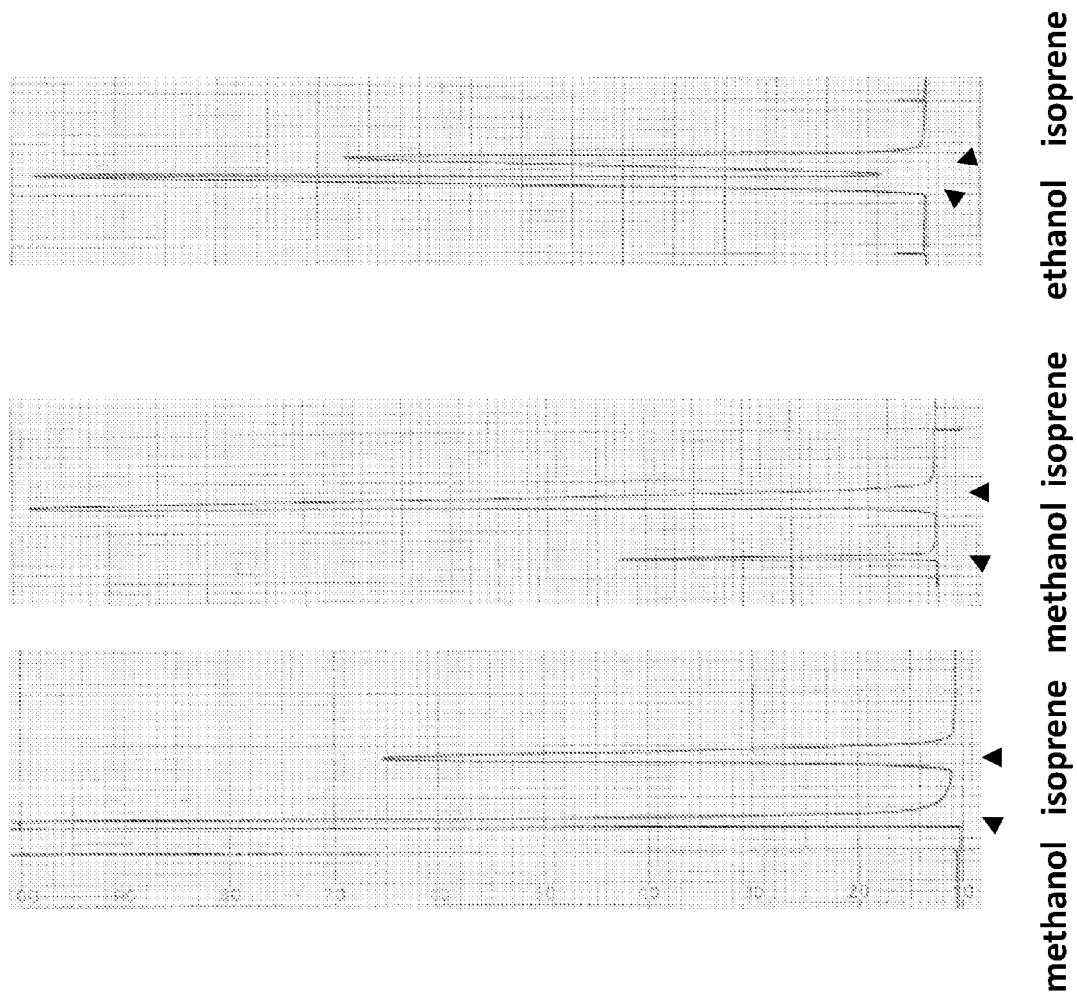
FIG. 9 provides an example of GC-FID analysis of solvent-isoprene blends. Shown are blends with different ratios of methanol/isoprene and ethanol/isoprene mixtures. Also tested with similar results were isoprene-butanol, isoprene-hexane, isoprene-heptane, isoprene-octane and isoprene-dodecane blends.

Photosynthetically generated isoprene and $O_2$ were periodically flushed out of the culture headspace upon slow bubbling with aliquots of 100% $CO_2$, as described for FIGS. 1 and 8. The mixture of gasses from the headspace were then passed through a Graham condenser cooled to 4° C., followed by passage of the condensed isoprene (boiling point 34.1° C.) and of the other gasses through an organic solvent. The mini-scale-up cultures were sealed each time after briefly bubbling with 100% $CO_2$ to refill the headspace, and culture growth resumed under constant illumination of 150 µmol photons $m^{-2}s^{-1}$ at 35° C. under gentle stirring to allow mixing and $CO_2$ diffusion-supported photoautotrophic growth. This step of periodic $CO_2$ bubbling and isoprene and $O_2$ removal was repeated as required, resulting in product (isoprene and $O_2$) removal from the headspace and replacement with $CO_2$. This protocol worked equally well with cyanobacterial or green microalgal cultures. Alcohols such as methanol (boiling point 64.7° C.), ethanol (boiling point 78.0° C.), butanol (boiling point 117.7° C.), and pure hydrocarbons such as hexane (boiling point 69.0° C.), heptane (boiling point 98.4° C.), octane (boiling point 125.5° C.), and dodecane (boiling point 216.2° C.) readily formed stable "blends" with isoprene (FIG. 9), thereby facilitating its retention and stabilization in a liquid solution. The diffusion-based process of carbon dioxide uptake and volatile product emission and sequestration in the headspace of gaseous/aqueous two-phase photobioreactors, and the subsequent trapping of volatile product upon cooling and blending with organic solvents that have a boiling point (temperature) greater than that of isoprene was successfully tested with cyanobacteria and green microalgae.

Discussion

Application of photosynthesis for the direct generation of fuel offers the advantage of a short cut in the solar-to-biofuel product generation process. It is based on the premise of a single organism acting both as photocatalyst and processor, entailing sunlight absorption and utilization, as well as $CO_2$ assimilation and conversion into product within a single host organism. This direct approach eliminates the need of a multistep process, whereby accumulation of intermediate feedstock, such as sugars or biomass is required.

Photosynthetic microorganisms, e.g. cyanobacteria and microalgae, are the organisms of choice for such direct solar-to-product processes, as they grow to high densities in sealed photobioreactors (Chisti, 2007; Angermayr et al., 2009; Beer et al., 2009), and have better solar energy conversion efficiencies in photosynthesis than land plants (Melis, 2009). When the targeted product is a small volatile molecule, such as isoprene, then the advantages are multiplied as the product is naturally separated from the biomass, eliminating the need for expensive dewatering of the culture, product extraction from within cells, and the inevitable lysis of the host organism. Isoprene is promising as a high-value bio-product, acting both as a chemical feedstock and a biofuel. It constitutes the building block of synthetic rubber and a number of adhesives, which are currently derived from petrochemical resources. Pure hydrocarbons store greater relative energy than alcohols (Schakel et al., 1997; Berg et al., 2002), making isoprene well suited for development as a drop-in biofuel. Commercial exploitation of this technology required that two further issues be resolved: (i) titre of isoprene production must be as high as possible, and (ii) a 'scale-up' method for isoprene generation, sequestration, and trapping be developed. Here, we have addressed the second of these two issues and described a diffusion-based method for gas exchange in gaseous/aqueous two-phase photobioreactors, using carbon dioxide as a feedstock for the photosynthetic generation and collection of isoprene.

Defining conditions that favoured $CO_2$ uptake and assimilation, and the production and sequestration of volatile isoprene in an enclosed bioreactor was important to this new method. Continuous bubbling of the culture and the simultaneous collection of isoprene in 'real time' was avoided, as the concentrations of isoprene in a continuous air-stream, or $CO_2$-stream, would be low. Additionally, continuous bubbling methods are cost-prohibitive in scale-up operations. Instead, a diffusion-based method for gas exchange in gaseous/aqueous two-phase photobioreactors was developed, where the headspace of the bioreactor was filled with 100% $CO_2$, sealed, and left in a resting stage, allowing the diffusion-based $CO_2$ uptake and assimilation by the cells via photosynthesis in the liquid phase, and the concomitant replacement of the $CO_2$ in the gaseous headspace with isoprene vapour and $O_2$. This approach allowed isoprene accumulation and sequestration in the headspace at much higher concentrations than would be achieved upon continuous bubbling. The physicochemical condensation of isoprene and subsequent trapping in solvents such as methanol, ethanol, butanol, hexane, heptane, octane and dodecane allowed the harvested isoprene to be retained as a stable blendstock.

Halling-Sorensen et al. (1996) employed airtight test flasks for testing the toxicity of volatile and hazardous chemicals (e.g. phenanthrene) with algae. Their procedure of airtight test flasks made it possible to maintain a constant and well-defined concentration of toxic compound in the sealed reactor during the entire test. They compared rates of growth of the green algae *Selenastrum capricornutum* in such airtight sealed testflasks with $NaHCO_3$ (12.5 mM) as a source of carbon in the growth medium and a $CO_2$ enriched headspace (1% $CO_2$) for balancing the pH. In their configuration, the $NaHCO_3/CO_2$ mol:mol ratio in the airtight test flasks was about 7:1, suggesting that $NaHCO_3$ is the primary inorganic carbon source for cell growth. They measured the rate of growth of the algae over 2 or 3 days in the absence or presence of phenanthrene, and reported that the obtained EC10 and EC50 values were 10 times lower with the airtight test flasks than those obtained with open test systems, thereby validating a method by which to test the toxicity of a variety of volatile and hazardous chemicals to living cells. Accordingly, the purpose of the airtight test flasks by Halling-Sorensen et al. (1996) was retention of the volatile phenanthrene inhibitor in the reactor, rather than product accumulation and sequestration.

In the experiments described here, the headspace of the bioreactor was filled with 100% $CO_2$, such that the high concentration of $CO_2$ supported growth of a proportionally larger culture volume for up to 2 days. Moreover, the gaseous/aqueous two-phase system employed in this work enabled isoprene product accumulation and sequestration, and further permitted the periodic delivery of supplemental aliquots of $CO_2$ as required, to overcome the carbon-limitation and to maintain high growth rates, coupled with high rates of isoprene biosynthesis, over longer periods of time.

Repetition of the carbon replenishing and isoprene harvesting protocol enabled cells to continuously produce isoprene but also to reach high biomass density in the bioreactor (FIG. 7). Accordingly, a continuous culturing method was devised and employed, which involved the periodic dilution of the culture to ensure it is always in the exponential phase of growth (FIG. 8). This practice ensured that the culture does not exceed a 0.7 g dw biomass per L culture. A medium density biomass mitigates the negative effects of reduced light penetration to cells that would prevail at high biomass density in photobioreactors (Mitra and Melis, 2008; Melis, 2009). The method described in this work thus allows cells to be maintained in a metabolically active state that is favorable for maximum rates of isoprene production over an indefinite period of time, and from which more concentrated forms of isoprene may be harvested from the reactor headspace. Indeed, consistent rates of isoprene production were measured over multiple dilutions in a continuous culture (FIG. 8). These results provide evidence that the SkIspS transgene is stably incorporated into the multiple copies of the *Synechocystis* genome, and retains stability of expression over multiple generations in the absence of antibiotic selection.

The method described in this work for the generation, sequestration, and trapping of photosynthetically derived isoprene hydrocarbons from a cyanobacterial or green microalgal culture is based on the principle of diffusion-driven gas exchange in a gaseous/aqueous two-phase photobioreactor, which operates in a sealed fed-batch or continuous culture mode.

REFERENCES

Angermayr S A, Hellingwerf K J, Lindblad P, Teixeira de Mattos M J, 2009. Energy biotechnology with cyanobacteria. Curr Opinion Biotech 20:257-263.

Beer L L, Boyd E S, Peters J W, Posewitz M C, 2009. Engineering algae for biohydrogen and biofuel production. Curr Opinion Biotech 20:264-271.

Behnke K, Ehlting B, Teuber M, Bauerfeind M, Louis S, Hänsch R, Polle A, Bohlmann J, Schnitzler J-P, 2007. Transgenic, non-isoprene emitting poplars don't like it hot. Plant J 51:485-499.

Berg J, Tymoczko J L, and Stryer L, 2002. Biochemistry (5th ed.), W. H. Freeman, San Francisco, Calif. p. 603. ISBN 0716746840.

Chisti Y, 2007. Biodiesel from microalgae. Biotechnology Advances 25:294-306.

Eaton-Rye J J, 2004. The construction of gene knockouts in the cyanobacterium *Synechocystis*sp. PCC 6803, in Methods of Molecular Biology, Vol 274: Photosynthesis Protocols (Carpentier, R., Ed.) pp 309-324, Humana Press, Totowa, N.J.

Fortunati A, Barta C, Brilli F, Centritto M, Zimmer I, Schnitzler J-P, Loreto F, 2008. Isoprene emission is not temperature-dependent during and after severe drought-stress: a physiological and biochemical analysis. Plant J 55:687-697.

Halling-Sorensen B, Nyholm N, Baun A, 1996. Algal toxicity tests with volatile and hazardous compounds in airtight test flasks with $CO_2$ enriched headspace. Chemosphere 32:1513-1526

Kuzma J, Nemecek-Marshall M, Pollock W H, Fall R, 1995. Bacteria produce the volatile hydrocarbon isoprene. Curr Microbiol 30:97-103.

Lichtenthaler H K, 1999. The 1-deoxy-D-xylulose-5-phosphate pathway of isoprenoid biosynthesis in plants. Annu Rev Plant Physiol Plant Mol Biol 50:47-65.

Lichtenthaler H K, 2000. Sterols and isoprenoids. Biochemical Society Transactions 28:785-789.

Lindberg P, Park S, Melis A, 2010. Engineering a platform for photosynthetic isoprene production in cyanobacteria, using *Synechocystis* as the model organism. Metabolic Engineering 12:70-79.

Meeks J C, Castenholz R W, 1971. Growth and photosynthesis in an extreme thermophile, *Synechococcus Lividus* (Cyanophyta). Arch Mikrobiol 78:25-41.

Melis A, 2009. Solar energy conversion efficiencies in photosynthesis: Minimizing the chlorophyll antenna to maximize efficiency. Plant Science 177:272-280.

Mgalobilishvili M P, Khetsuriani N D, Kalandadze A N, Sanadze G A, 1978. Localization of isoprene biosynthesis in poplar leaf chloroplasts. Fiziol Rast 25:1055-1061.

Miller B, Oschinski C, Zimmer W, 2001. First isolation of an isoprene synthase gene from poplar and successful expression of the gene in *Escherichia coli*. Planta 213:483-487.

Mitra M, Melis A, 2008. Optical properties of microalgae for enhanced biofuels production. Optics Express 16:21807-21820.

Mitra M, Melis A, 2010. Genetic and biochemical analysis of the TLA1 gene in *Chlamydomonas reinhardtii*. Planta 231:729-740

Rohmer M, Seemann M, Horbach S, Bringer-Meyer S, Sahm, H, 1996. Glyceraldehyde 3-phosphate and pyruvate as precursors of isoprenic units in an alternative non-mevalonate pathway for terpenoid biosynthesis. J Am Chem Soc 118: 2564-2566.

Sanadze G A, 1969. Light-dependent excretion of molecular isoprene. Prog Photosynth Res 2:701-707.

Sanadze G A, Dzhaiani G I, Tevzadze I M, 1972. Incorporation into the isoprene molecule of carbon from $^{13}CO_2$ assimilated during photosynthesis. Soy Plant Physiol 19:17-20.

Sasaki K, Ohara K, Yazaki K, 2005. Gene expression and characterization of isoprene synthase from *Populus alba*. FEBS Lett 579:2514-2518.

Sasaki K, Saito T, Lamsa M, Oksman-Caldentey K M, Suzuki M, Ohyama K, Muranaka T, Ohara K, Yazaki K, 2007. Plants utilize isoprene emission as a thermotolerance mechanism. Plant Cell Physiol 48:1254-1262.

Schakel S F, Buzzard I M, Gebhardt S E, 1997. Procedures for estimating nutrient values for food composition databases. J Food Comp Anal 10:102-114.

Sharkey T D, Yeh S, 2001. Isoprene emission from plants Annu Rev Plant Physiol 52:407-36.

Sharkey T D, Chen X Y, Yeh S, 2001. Isoprene increases thermotolerance of fosmidomycin-fed leaves. Plant Physiol 125: 2001-2006

Sharkey T D, Yeh S, Wiberley A E, Falbel T G, Gong D, Fernandez D E, 2005. Evolution of the isoprene biosynthetic pathway in kudzu. Plant Physiol 137:700-712.

Sharkey T D, Wiberley A E, Donohue A R, 2008. Isoprene emission from plants: why and how. Annals of Botany 101: 5-18.

Silver G M, Fall R, 1991. Enzymatic synthesis of isoprene from dimethylallyl diphosphate in aspen leaf extracts. Plant Physiol 97:1588-1591.

Singaas E L, Lerdau M T, Winter K, Sharkey T D, 1997. Isoprene increases thermotolerance of isoprene-emitting species. Plant Physiol 115:1413-1420.

Whited G M, Feher F J, Benko D A, Cervin M A, Chotani G K, McAuliffe J C, LaDuca R J, Ben-Shoshan E A, Sanford K J, 2010. Development of a gas-phase bioprocess for isoprene-monomer production using metabolic pathway engineering. Industrial Biotech 6:152-163.

Williams J G K, 1988. Construction of specific mutations in photosystem II photosynthetic reaction center by genetic engineering methods in *Synechocystis* 6803. Methods Enzymol 167:766-778.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A continous method of cultivating photosynthetic microorganisms in a sealed photobioreactor to obtain a volatile hydrocarbon product of photosynthesis generated by the microorganisms, the method comprising
   (i) culturing a photosynthetic microorganism in light in a sealed photobioreactor, wherein the photobioreactor contains a lower aqueous phase comprising the photosynthetic microorganism, and an upper gaseous phase, wherein the upper gaseous phase comprises $CO_2$ that is introduced from outside of the photobioreactor through a port into the photobioreactor as a source of carbon for the photosynthetic microorganisms, wherein the $CO_2$ is introduced to provide a concentration in the upper gaseous phase of at least 10%;
   (ii) collecting from the gaseous phase the volatile hydrocarbon produced by the microorganism that diffuses into the gaseous phase;
   (iii) introducing additional $CO_2$ from outside of the photobioreactor into the upper gaseous phase to replace $CO_2$ that is consumed by the photosynthetic microorganisms, wherein the additional $CO_2$ is introduced to provide a concentration of at least 10%.

2. The method of claim 1, wherein the photosynthetic microorganism is a recombinant organism that expresses at least one heterologous gene that produces the volatile hydrocarbon.

3. The method of claim 2, wherein the volatile hydrocarbon product is isoprene.

4. The method of claim 3, wherein the microorganism expresses an isoprene synthase gene.

5. The method of claim 1, wherein the microorganism is a cyanobacteria.

6. The method of claim 1, wherein the microorganism is a green microalgae.

7. The method of claim 1, wherein the volatile hydrocarbon product is an alcohol.

8. The method of claim 7, wherein the alcohol is ethanol, butanol or isobutanol.

9. The method of claim 1, wherein the volatile hydrocarbon product is an aldehyde.

10. The method of claim 9, wherein the aldehyde is acetaldehyde, butyraldehyde, or isobutyraldehyde.

11. The method of claim 1, wherein the volume ratio of the gaseous phase to the aqueous phase is in the range of from about 1:9 to about 9:1.

12. The method of claim 11, wherein the volume ratio of the gaseous phase to the aqueous phase is in the range of from about 4:6 to about 6:4.

13. The method of claim 2, wherein the volume ratio of the gaseous phase to the aqueous phase is in the range of from about 1:9 to about 9:1 or from about 4:6 to about 6:4.

14. The method of claim 1, wherein the volatile hydrocarbon product is isoprene and the step of collecting the isoprene comprises passing the contents of the gaseous phase, through a cooled condenser and through a cooled hydrophobic solvent, thereby retaining the isoprene and separating it from the photosynthetically-generated $O_2$.

15. The method of claim 14, wherein the hydrophobic solvent comprises methanol, ethanol, butanol, hexane, heptane, octane, or dodecane.

16. The method of claim 2, wherein the volatile hydrocarbon product is isoprene and the step of collecting the isoprene comprises passing the contents of the gaseous phase, through a cooled condenser and through a cooled hydrophobic solvent, thereby retaining the isoprene and separating it from the photosynthetically-generated $O_2$.

17. The method of claim 16 wherein the hydrophobic solvent comprises methanol, ethanol, butanol, hexane, heptane, octane, or dodecane.

18. The method of claim 1, wherein the $CO_2$ introduced in (i) provides a concentration in the upper gaseous phase of at least 50%.

19. The method of claim 18, wherein the step of introducing additional $CO_2$ into the upper gaseous phase provides a $CO_2$ concentration of at least 50%.

20. The method of claim 1, wherein the $CO_2$ introduced in (i) provides a concentration in the upper gaseous phase of at least 90%.

21. The method of claim 20, wherein the step of introducing additional $CO_2$ into the upper gaseous phase provides a $CO_2$ concentration of at least 90%.

22. The method of claim 1, wherein step (iii) is performed concurrently with step (ii).

* * * * *